United States Patent [19]
Gschwend et al.

[11] 3,941,883
[45] Mar. 2, 1976

[54] AROMATIC DICARBOXAMIDES AS ANTICONVULSANTS
[75] Inventors: Heinz Werner Gschwend, New Providence; Malvin J. Hillman, Bloomfield, both of N.J.
[73] Assignee: Ciba-Geigy Corporation, Ardsley, N.Y.
[22] Filed: Mar. 11, 1974
[21] Appl. No.: 449,872

[52] U.S. Cl....... 424/274; 260/239.3 B; 260/281 N; 260/295 AM; 260/326 N; 260/326 S; 260/326.5 D; 260/326.5 S; 424/244; 424/263; 424/267; 424/275; 424/285
[51] Int. Cl.² .......................................... A61K 31/40
[58] Field of Search................ 260/326 N; 424/274

[56] References Cited
UNITED STATES PATENTS
3,767,805  10/1973  Carney et al. ..................... 424/274

Primary Examiner—Stanley J. Friedman
Attorney, Agent, or Firm—Joseph G. Kolodny; Theodore O. Groeger; John J. Maitner

[57] ABSTRACT
N-(4-aminophenyl)-aromatic dicarboxamides, e.g., those of the formula

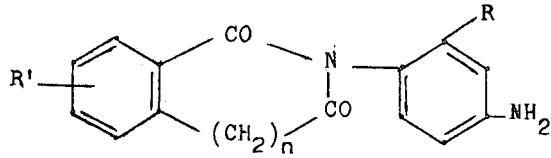

R = alkyl, (hydroxy, alkoxy, alkylmercapto-sulfinyl or -sulfonyl)-alkyl, halogeno or $CF_3$ R' = alkyl, alkoxy, alkylmercapto, -sulfinyl or -sulfonyl, halogeno, $CF_3$, carbamoyl or sulfamoyl n = 0 or 1 or salts thereof are anticonvulsants.

4 Claims, No Drawings

AROMATIC DICARBOXAMIDES AS ANTICONVULSANTS

BACKGROUND OF THE INVENTION

Compounds of the above formula, wherein at least one of R and R' is hydrogen, are disclosed in U.S. Pat. No. 3,767,805 or British Pat. No. 901,420 as intermediates in the preparation of "α-(cyclic tert. aminophenyl)-aliphatic acids" or "azo coloring matters" respectively. Surprisingly it was found that by properly selecting substituents and their relative positions within the aromatic nuclei of said dicarboximides, highly potent anticonvulsant agents are obtained.

SUMMARY OF THE INVENTION

The present invention concerns and has for its object the provision of novel N-(4-aminophenyl)-aromatic dicarboximides, more particularly of those corresponding to Formula I

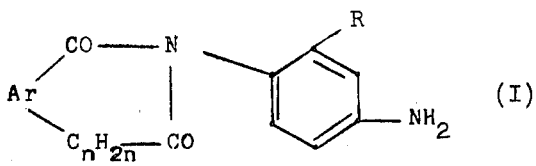

wherein Ar is 1,2-phenylene substituted by at least one member selected from lower alkyl, alkoxy, alkylmercapto, -sulfinyl or -sulfonyl, halogeno, trifluoromethyl, carbamoyl, sulfamoyl, mono- or dialkylcarbamoyl or -sulfamoyl; unsubstituted or alkylated and/or halogenated 2,3- or 3,4-(furylene, thienylene or pyridylene), R is lower alkyl, (hydroxy, alkoxy, alkylmercapto, -sulfinyl or -sulfonyl)-alkyl, halogeno or trifluoromethyl, $n$ is an integer from 0 to 3 and $C_nH_{2n}$ separates Ar from CO by one or no carbon atom, or acid addition salts thereof, as well as of corresponding pharmaceutical compositions and of methods for the preparation and application of these products, which are useful anticonvulsant agents, for example in the treatment or management of epilepsy or other spastic conditions.

DESCRIPTION OF THE PREFERRED EMBODIMENTS

The 1,2-phenylene radical Ar, is preferably substituted by one or two, of the same or different members selected from, e.g., methyl, ethyl, n- or i-propyl or -butyl; methoxy, ethoxy, n- or i-propoxy or -butoxy; (methyl or ethyl)-(mercapto, sulfinyl or sulfonyl); fluoro, chloro or bromo; trifluoromethyl; carbamoyl, sulfamoyl, mono- or di-(methyl or ethyl)-(carbamoyl or sulfamoyl). The 2,3- or 3,4-(furylene, thienylene or pyridylene) radicals Ar are preferably unsubstituted, or may contain one or two of the same or different members selected from methyl, ethyl, fluoro or chloro, for example.

The lower alkyl group or halogen atom R is preferably methyl, ethyl, fluoro, chloro, or bromo but also one of the other respective members listed above and the substituted lower alkyl group R is preferably α-(hydroxy, methoxy, ethoxy, methyl- or ethylmercapto, -sulfinyl or -sulfonyl)-(methyl or ethyl). The term "lower," referred to above and hereinafter in connection with organic radicals or compounds respectively, defines such with up to seven, preferably up to four, especially up to two carbon atoms.

The acid addition salts of the amines of Formula I are preferably those of the therapeutically useful acids listed below.

The compounds of the invention exhibit valuable pharmacological properties, primarily anticonvulsant activity, as can be demonstrated in animal tests, using advantageously mammals, such as mice or rats, as test objects. Said compounds can be applied to the host suffering from agitation and/or convulsions either enterally or parenterally, e.g., orally or intraperitoneally, for example in the form of aqueous solutions or starchy suspensions. The oral or intraperitoneal dosage may range between about 1 and about 800 mg/kg/day, preferably between about 5 and 500 mg/kg/day or especially between about 10 and about 50 mg/kg/day. Anticonvulsant effects are observed, for example, by the protection of said mammals against electrically or chemically induced seizures, such as mouse or rat minimum or maximum electroshock, or seizures caused by 1,5-pentamethylenetetrazole, picrotoxin, thiosemicarbazide or strychnine. According to the former test the compounds of the invention, for example, the N-(4-amino-o-tolyl)-4-chlorophthalimide, an illustrative member thereof, are administered to the animals either orally or intraperitoneally and 1 or 2 hours later, preferably at peak effect, they are given an electric shock, e.g., to mice 50 milliamperes of current and 0.2 second duration through corneal electrodes, from which all animals recover. Those animals not exhibiting a tonic (hind limb) extensor seizure are considered protected.

They are also given the compounds of the invention, either orally or intraperitoneally, and 1 hour later, for example, 24 mg/kg 1,5-pentamethylenetetrazole intravenously to rats. They are checked immediately for the presence of clonic seizures and all animals not exhibiting them are also considered protected. Furthermore, the overt effects of the compounds of Formula I are observed in rats ½, 1, 2 and 20 hours after various oral or intraperitoneal doses and $ED_{50}$ values are estimated for various effects, e.g., muscle tone or ataxia, indicating skeletal muscle relaxing activity. According to the test results observed, the compounds of the invention are useful anticonvulsant agents, for example in the treatment or management of epilepsy or other spastic conditions. They are also useful intermediates in the preparation of other valuable products, preferably of pharmacologically active compounds, e.g., the anti-inflammatory agents mentioned above.

Preferred compounds of the invention are those of Formula I, wherein Ar is 1,2-phenylene substituted by one or two of the same or different members selected from lower alkyl, alkoxy, alkylmercapto, -sulfinyl or -sulfonyl, halogeno, trifluoromethyl, carbamoyl, sulfamoyl, mono- or dialkylcarbamoyl or -sulfamoyl, unsubstituted, mono- or bis- lower alkylated and/or halogenated 2,3- or 3,4-(furylene, thienylene or pyridylene), R is lower alkyl, lower α-(hydroxy, alkoxy, alkylmercapto, -sulfinyl or -sulfonyl)-alkyl, halogeno or trifluoromethyl and $n$ is the integer 0 or 1, or a therapeutically acceptable acid addition salt thereof.

More preferred on account of their anticonvulsant effects are those compounds of Formula I, wherein Ar is 1,2-phenylene substituted by one or two of the same or different members selected from methyl, ethyl, methoxy, ethoxy, (methyl or ethyl)-(mercapto, sulfinyl or sulfonyl), fluoro, chloro, bromo, trifluoromethyl, carbamoyl, sulfamoyl, mono or di-(methyl or ethyl)-(carbamoyl or sulfamoyl); unsubstituted or mono- or di-(methyl, ethyl, fluoro or chloro)-substituted 2,3- or 3,4-(furylene, thienylene or pyridylene), R is methyl, ethyl, fluoro, chloro, bromo, trifluoromethyl or α-(hydroxy, methoxy, ethoxy, methyl- or ethylmercapto, -sulfinyl or -sulfonyl)-(methyl or ethyl) and $n$ is the integer 0 or 1, or a therapeutically acceptable and addition salt thereof.

Outstanding activity is exhibited by compounds of Formula II

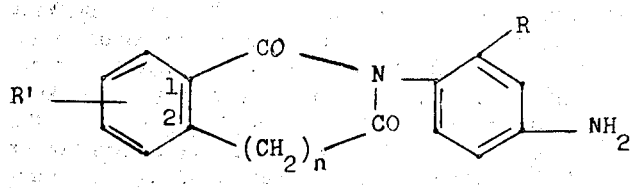

wherein R is methyl or ethyl, R' is methyl, ethyl, fluoro, chloro, bromo or trifluoromethyl and $n$ is the integer 0 or 1, or a therapeutically acceptable acid addition salt thereof.

Of special value are those compounds of Formula II, wherein R is methyl, R' is methyl, fluoro, chloro, bromo or trifluoromethyl, preferably in the 4-position, and $n$ is zero, or a therapeutically acceptable acid addition salt thereof.

The compounds of the invention are prepared according to methods known per se. For example, they are obtained by converting in a compound of Formula III

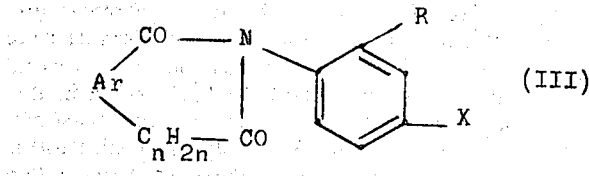

wherein X is a nitro, azido, azo, isocyanato or an acylamino group, X into amino by reduction or hydrolysis respectively and, if desired, converting any resulting compound into another compound of the invention.

An azo and acylamino group X is preferably derived from an isocyclic aromatic radical, e.g., phenyl or H—Ar, or a lower alkanoic or aralkanoic acid or carbonic acid half-ester. Preferred radicals X are: $NO_2$, $N_3$, $C_6H_5$—$N_2$; NCO, $C_mH_{2m+1}$—CONH, $C_mH_{2m+1}$—OCONH or $C_6H_5$—CONH, wherein $m$ is 1 to 7. The former groups are converted into amino by conventional reduction, for example, with the use of catalytically activated or nascent hydrogen, e.g., hydrogen in the presence of platinum, palladium or nickel catalysts, e.g., Raney nickel, or generated by the action of non-precious metals, e.g., zinc or iron, on acids, such as mineral acids, e.g., hydrochloric or sulfuric acid, or with the use of reducing agents, preferably salts or elements of the 4th to 6th group of the Periodic Table and being in a low oxidation state, such as titanous, stannous or chromous halides, ammonium polysulfides or alkali metal hydrosulfites. The latter acylated amino groups are converted into amino by acidic or basic hydrolysis, the isocyanato group (for example formed in the course of the Schmidt-reaction) preferably with strong inorganic acids, such as hydrochloric, sulfuric or phosphoric acid, and the other acylamino groups preferably with the use of aqueous bases, such as aqueous alkali metal hydroxides or carbonates, or quaternary ammonium hydroxides, e.g., sodium hydroxide, potassium carbonate or trimethylbenzyl-ammonium hydroxide.

The compounds of the invention so obtained can be converted into each other according to methods known per se. For example, resulting hydroxyalkyl compounds, preferably acid addition salts thereof, can be etherified with lower alkyl halides or sulfates to corresponding compounds of Formula I, wherein R is lower alkoxyalkyl. Moreover, resulting alkylmercapto-products can be oxidized, advantageously with the use of alkali metal periodates or perbenzoic acid, to yield corresponding alkylsulfinyl or -sulfonyl compounds, or carbamoyl or sulfamoyl-products may be treated under strong alkaline conditions with said esters of lower alkanols, to yield the N-alkylated derivatives thereof.

A resulting basic compound can be converted into a corresponding acid addition salt, for example by reacting it with an inorganic or organic acid, such as a therapeutically useful acid, or with a corresponding anion exchange preparation, and isolating the desired salt. An acid addition salt may be converted into the free compound by treatment with a base, e.g., a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g., carboxylic or sulfonic acids, such as formic, acetic, propionic, succinic, glycollic, lactic, malic, tartaric, citric, ascorbic, maleic, hydroxymaleic, pyruvic, phenylacetic, benzoic, 4-aminobenzoic, anthranilic, 4-hydroxybenzoic, salicylic, aminosalicylic, pamoic, nicotinic, methanesulfonic, ethanesulfonic, hydroxyethanesulfonic, ethylenesulfonic, benzenesulfonic, halogenbenzenesulfonic, toluenesulfonic, naphthalenesulfonic, sulfanilic, or cyclohexylsulfamic acid.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Resulting mixtures of isomers can be separated into the single isomers by methods in themselves known, e.g., by fractional distillation, crystallization and/or chromatography. Racemic products can likewise be resolved into the optical antipodes, for example by separation of diastereomeric salts thereof, e.g., by the fractional crystallization of d- or l-tartrates.

The above reactions are carried out according to standard methods, in the presence or absence of diluents, preferably such as are inert to the reagents and are solvents thereof, of catalysts, condensing or neutralizing agents and/or inert atmospheres, at low temperatures, room temperature or elevated temperatures, at atmospheric or superatmospheric pressure.

The invention also comprises any modification of the above process, wherein a compound resulting as an intermediate at any stage thereof, is used as starting material and the remaining steps are carried out, or the process is discontinued at any stage thereof, or in which the starting material is formed under the reaction conditions or is used in the form of its salts or reactive derivatives. As mentioned above, isocyanates are formed from the corresponding acid azides and acylamino compounds may be formed in the formation of the cyclic starting materials from their acyclic precursors. In the process of the invention, those starting materials are advantageously selected, which yield the above-described preferred embodiments of the invention, especially those corresponding to Formula II.

The starting material used is known or, if new, can be prepared according to the methods described for known analogs thereof, or by the methods illustrated in the examples herein.

The pharmacologically active compounds of the invention are useful in the manufacture of pharmaceutical compositions containing an effective amount thereof in conjunction or admixture with excipients suitable for either enteral, parenteral or topical application. Preferred are tablets and gelatin capsules comprising the active ingredient together with (a) diluents, e.g., lactose, dextrose, sucrose, mannitol, sorbitol, cellulose and/or glycine, (b) lubricants, e.g., silica, talcum, stearic acid, its magnesium or calcium salt and/or polyethyleneglycol, for tablets also (c) binders, e.g., magnesium aluminum silicate, starch paste, gelatin, tragacanth, methylcellulose, sodium carboxymethylcellulose and/or polyvinylpyrrolidone, if desired, (d) disintegrants, e.g., starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously made from fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively and contain about 0.1 to 75%, preferably about 1 to 50% of the active ingredient.

The following examples are intended to illustrate the invention and are not to be construed as being limitations thereon. Temperatures are given in degrees centigrade, all parts wherever given are parts by weight, and all evaporations are carried out under reduced pressure.

EXAMPLE 1

The mixture of 3.94 g of N-(4-nitro-o-tolyl)-3-methylphthalimide, 200 ml of ethyl acetate and 2.2 g of Raney nickel (pre-washed with water and ethyl acetate) is hydrogenated at 3.1 atm. and room temperature until the hydrogen uptake ceases. It is filtered, evaporated, the residue triturated with chloroform, filtered again, the filtrate evaporated and the residue recrystallized from methanol, to yield the N-(4-amino-o-tolyl)-3-methylphthalimide of the formula

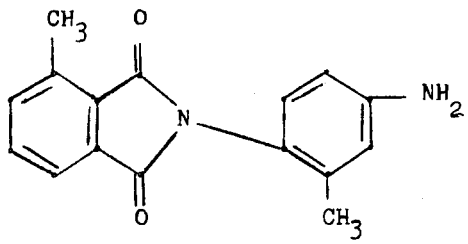

melting at 209°–211°.

The starting material is prepared as follows: The mixture of 16.2 g of 3-methylphthalic anhydride, 15.2 g of 4-nitro-o-toluidine and 400 ml of xylene is refluxed for 2 days and evaporated. The residue is taken up in 400 ml of acetic anhydride and the mixture refluxed for 18 hours. It is evaporated and the residue recrystallized from ethanol, to yield the N-(4-nitro-o-tolyl)-3-methylphthalimide, melting at 195°–199°.

EXAMPLE 2

The mixture of 4.28 g of N-(4-nitro-o-tolyl)-4-methylphthalimide, 200 ml of 95% aqueous ethanol and 0.21 g of 5% palladium on charcoal is hydrogenated at 3.1 atm and 45° until the hydrogen uptake ceases. The resulting suspension is diluted with the minimum amount of dimethylformamide to solubilize the organic material, filtered and evaporated. The residue is taken up in chloroform, the mixture filtered, evaporated and the residue recrystallized from methanol, to yield the N-(4-amino-o-tolyl)-4-methylphthalimide melting at 144°–147°.

The staring material is prepared as follows: The mixture of 5.0 g of 4-methylphthalic anhydride, 4.7 g of 4-nitro-o-toluidine and 100 ml of xylene is refluxed for 2½ days on a water trap. It is evaporated and the residue recrystallized from ethanol, to yield the N-(4-nitro-o-tolyl)-4-methylphthalimide melting at 184°–186°.

EXAMPLE 3

The mixture of 1.65 g of N-(4-nitro-o-tolyl)-3-chlorophthalimide, 200 ml of ethyl acetate and 0.92 g of pre-washed Raney nickel is hydrogenated at 3.1 atm. and room temperature until the hydrogen uptake ceases. It is filtered, evaporated and the residue recrystallized from methanol, to yield the N-(4-amino-o-tolyl)-3-chlorophthalimide melting at 209°–211°.

The starting material is prepared as follows: The mixture of 3-chlorophthalic anhydride, 2.5 g of 4-nitro-o-toluidine and 200 ml of xylene is refluxed for 2 days on a water-trap and evaporated. The residue is taken up in chloroform, the mixture filtered, the filtrate chromatographed on silica gel and the column eluted with chloroform-ethyl acetate (9:1), to yield the N-(4-nitro-o-tolyl)-3-chlorophthalimide melting at 229°–232°.

EXAMPLE 4

The mixture of 12.4 g of N-(4-nitro-o-tolyl)-4-chlorophthalimide, 1.0 lt. ethyl acetate and 10 ml of an ethanolic suspension containing 6.9 g of Raney nickel is hydrogenated at 2.8 atm. and room temperature for 12 hours. It is filtered, concentrated to about half of its original volume and the precipitate formed collected, to yield the N-(4-amino-o-tolyl)-4-chlorophthalimide melting at 201°–203°. Its 4-bromo-analog melts at 208°–211°.

The starting material is prepared as follows: The mixture of 36 g of 4-chlorophthalic acid and 250 ml of acetic anhydride is refluxed for 2 hours and evaporated. The residual 4-chlorophthalic anhydride is dried in a high vacuum and 27.8 g thereof refluxed in 480 ml of toluene together with 23.1 g of 4-nitro-o-toluidine for 1 day. It is cooled the precipitate filtered off, washed with benzene and dried at 80°/0.1 mmHg, to yield the corresponding amide melting at 185°–188°.

The mixture of 35 g thereof and 250 ml of acetic anhydride is refluxed for 2 hours and evaporated. The residue is dried, taken up in the minimum amount of hot ethyl acetate, the solution treated with charcoal, filtered, the filtrate cooled and the precipitate formed collected, to yield N-(4-nitro-o-tolyl)-4 chlorophthalimide melting at 221°–222°.

EXAMPLE 5

The mixture of 35.9 g of N-(4-nitro-o-tolyl)-tetrachlorophthalimide, 250 ml of dimethylformamide and 0.32 g of 5% platinum oxide is hydrogenated at room temperature and atmospheric pressure for 2½ days. It is filtered, evaporated, the residue triturated with hot xylene, filtered, the filtrate evaporated and the residue recrystallized from ethanol, to yield the N-(4-amino-o-tolyl)-tetrochlorophthalimide melting at 166°–171° with decomposition.

The starting material is prepared as follows: The mixture of 28.6 g of tetrachlorophtalic anhydride, 15.2 g of 4-nitro-o-toluidine and 200 ml of xylene is refluxed for 2½ days on a water trap. It is cooled, the precipitate formed filtered off and recrystallized from methyl ethyl ketone, to yield the N-(4-nitro-o-tolyl)-tetrachlorophtalimide melting at 226°–230°.

EXAMPLE 6

The mixture of 10.0 g of N-(4-nitro-o-tolyl)-4-fluorophthalimide, 500 ml of ethyl acetate and 5 g of Raney nickel is hydrogenated at 3.1 atm. and room temperature until the hydrogen uptake ceases. It is filtered, evaporated and the residue recrystallized from ethanol, to yiedl the N-(4-amino-o-tolyl)-4-fluorophthalimide, melting at 180°–182°.

The starting material is prepared as follows: The mixture of 6.8 g of 4-fluorophthalic anhydride, 6.2 g of 4-nitro-o-foluidine and 160 ml of xylene is refluxed for 4 days at a water trap. It is evaporated, the residue taken up in 150 ml of acetic anhydride and the solution refluxed for 5 hours. It is evaporated and the residue recrystallized from n-propanol, to yield the N-(4-nitro-o-tolyl)-4-fluorophthalimide melting at 166°–168.5°.

EXAMPLE 7

The mixture of 3.55 g of N-(4-nitro-o-tolyl)-4-trifluoromethylphthalimide, 200 ml of 95% aqueous ethanol and 0.18 g of 5% palladium on carbon is hydrogenated at 3.1 atm. and 45° until the hydrogen uptake ceases. It is filtered, evaporated and the residue recrystallized from ethanol, to yield the N-(4-amino-o-tolyl)-4-trifluoromethylphthalimide melting at 161°–163°.

The starting material is prepared as follows: The mixture of 13.0 g of 4-trifluoromethylphthalic anhydride, 3.16 g of 4-nitro-o-toluidine and 100 ml of xylene is refluxed for 2½ days at a water trap. It is evaporated and the residue recrystallized from ethanol, to yield the N-(4-nitro-o-tolyl)-4-trifluoromethylphthalimide melting at 156°–158°.

EXAMPLE 8

The mixture of 2.83 g of N-(4-nitro-o-tolyl)-pyridine-2,3-dicarboximide, 200 ml of ethyl acetate and 1.6 g of prewashed Raney nickel is hydrogenated at 3.1 atm. and room temperature until the hydrogen uptake ceases. It is filtered, evaporated, the residue taken up in chloroform, the solution treated with charcoal, filtered, evaporated and the residue recrystallized from methanol, to yield the N-(4-amino-o-tolyl)-pyridine-2,3-dicarboximide of the formula

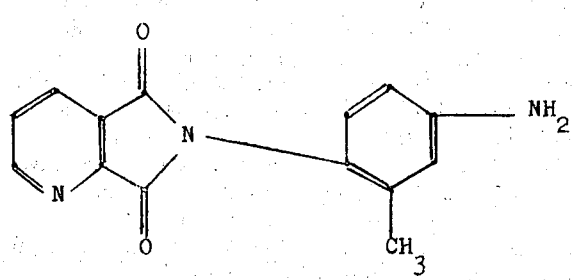

melting at 180°–182°.

The starting material is prepared as follows: The mixture of 10.0 g of pyridine-2,3-dicarboxylic anhydride, 10.3 g of 4-nitro-o-toluidine and 250 ml of xylene is refluxed for 2 days. It is evaporated, the residue taken up in 250 ml of acetic anhydride and the mixture refluxed for 5 hours. It is evaporated, the residue triturated with hot ethanol and the insoluble material recrystallized from ethyl acetate, to yield the N-(4-nitro-o-tolyl)-pyridine-2,3-dicarboximide melting at 223°–225°.

EXAMPLE 9

Preparation of 10,000 tablets each containing 100.0 mg of the active ingredient:

Formula:

| | |
|---|---|
| N-(4-amino-o-tolyl)-4-chlorophthalimide | 1,000.00 g |
| Lactose | 2,535.00 g |
| Corn starch | 125.00 g |
| Polyethylene glycol 6,000 | 150.00 g |
| Talcum powder | 150.00 g |
| Magnesium stearate | 40.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the posders which are granulated, if necessary, with an additional amount of water. The granulate is dried overnight at 35°, broken on a screen with 1.2 mm openings and compressed into tablets using concave punches with 10.3 mm diameter, uppers bisected.

In the analogous manner tablets are prepared, containing any of the other compounds of the invention, preferably those illustrated by the preceding examples herein.

We claim:

1. An anticonvulsant pharmaceutical composition in the form of a tablet or capsule comprising a spasmolytically effective amount of a compound corresponding to the formula

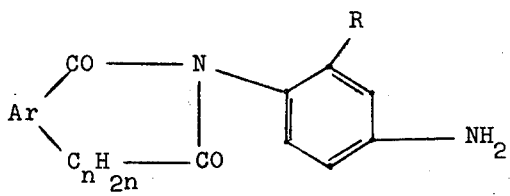

wherein Ar is 1,2-phenylene substituted by at least one member selected from lower alkyl, alkoxy, alkylmercapto, -sulfinyl or -sulfonyl, halogeno, trifluoromethyl, carbamoyl, sulfamoyl, mono- or dialkylcarbamoyl or -sulfamoyl; unsubstituted or alkylated and/or halogenated 2,3- or 3,4-(furylene, thienylene or pyridylene), R is lower alkyl, (hydroxy, alkoxy, alkylmercapto, -sulfinyl or -sulfonyl)-alkyl, halogeno or trifluoromethyl, $n$ is 0 and $C_nH_{2n}$ separates Ar from CO by one or no carbon atom, or acid addition salts thereof, together with a pharmaceutical excipient.

2. A composition as claimed in claim 1, wherein the effective compound corresponds to the formula

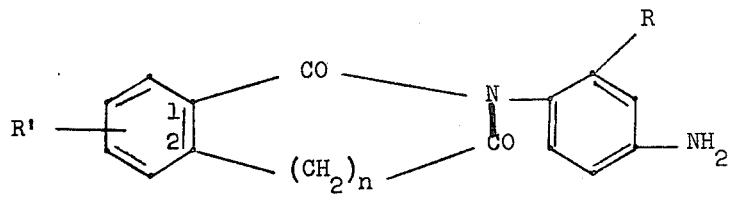

wherein R is methyl or ethyl, R' is methyl, ethyl, fluoro, chloro, bromo or trifluoromethyl and $n$ is the integer 0, or a therapeutically acceptable acid addition salt thereof.

3. A composition as claimed in claim 1, wherein the effective compound is the N-(4-amino-o-tolyl)-4-chlorophthalimide, or a therapeutically acceptable acid addition salt thereof.

4. A method for treating agitation and/or convulsions in a mammal, which consists in administering to said mammal enterally or parenterally a composition as claimed in claim 1.

* * * * *